US012697165B2

(12) United States Patent  
    Holzer et al.

(10) Patent No.:    US 12,697,165 B2  
(45) Date of Patent:      Aug. 4, 2026

(54) ACTUATING ELEMENT, SURGICAL INSTRUMENT, AND METHOD FOR MANUFACTURING THE ACTUATING INSTRUMENT

(71) Applicant: KARL STORZ SE & Co. KG, Tuttlingen (DE)

(72) Inventors: Judith Holzer, Tuttlingen (DE); Daniel Kärcher, Tuttlingen (DE); Dominik Längle, Tuttlingen (DE); Robin Merz, Tuttlingen (DE); Janosz Schneider, Tuttlingen (DE); Sven Schneider, Tuttlingen (DE); Tobias Unger, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 98 days.

(21) Appl. No.: 18/283,238

(22) PCT Filed: Jun. 22, 2022

(86) PCT No.: PCT/EP2022/066938  
§ 371 (c)(1),  
(2) Date: Sep. 21, 2023

(87) PCT Pub. No.: WO2022/268846  
PCT Pub. Date: Dec. 29, 2022

(65) Prior Publication Data  
US 2024/0285336 A1     Aug. 29, 2024

(30) Foreign Application Priority Data  
Jun. 23, 2021    (DE) ..................... 10 2021 116 216.5

(51) Int. Cl.  
   A61B 18/14        (2006.01)  
   A61B 17/00        (2006.01)  
   (Continued)

(52) U.S. Cl.  
   CPC .............................. *A61B 18/1447* (2013.01); *A61B 2017/00526* (2013.01); *A61B 2017/2902* (2013.01);  
   (Continued)

(58) Field of Classification Search  
   CPC .. A61B 2017/2902; A61B 2018/00196; A61B 2018/00202; A61B 2018/0091;  
   (Continued)

(56) References Cited

U.S. PATENT DOCUMENTS 4,128,099 A * 12/1978 Bauer ................ A61B 18/1445  
                                  606/52  
2007/0163106 A1* 7/2007 Mumford ............... A61B 5/296  
                                  29/746  
(Continued)

FOREIGN PATENT DOCUMENTS

CN       209404943 U     9/2019  
CN       210631299 U     5/2020  
(Continued)

OTHER PUBLICATIONS

International Search Report for International Application No. PCT/EP2022/066938, mailed Oct. 6, 2022.  
(Continued)

*Primary Examiner* — Jaymi E Della  
(74) *Attorney, Agent, or Firm* — Jason H. Vick; Amped IP LLC

(57) ABSTRACT  
This invention pertains to a force transmission element with combined mechanical support and electrical isolation, as well as a surgical instrument comprising the force transmission element and a method for manufacturing the force transmission element. A rod of the force transmission element has at least one recess and insulation extends at least along the recess. A sleeve of the force transmission element has an embossment that extends at least in sections into the (Continued)

recess and which is designed to mesh with a securing element of the surgical instrument.

6 Claims, 6 Drawing Sheets

(51) Int. Cl.

| | |
|---|---|
| *A61B 17/29* | (2006.01) |
| *A61B 18/00* | (2006.01) |
| *A61B 18/12* | (2006.01) |

(52) U.S. Cl.
CPC ............... *A61B 2018/00077* (2013.01); *A61B 2018/00083* (2013.01); *A61B 2018/00196* (2013.01); *A61B 2018/00202* (2013.01); *A61B 2018/0091* (2013.01); *A61B 2018/126* (2013.01)

(58) Field of Classification Search
CPC .......... A61B 2018/126; A61B 18/1445; A61B 18/1447
See application file for complete search history.

(56) References Cited

U.S. PATENT DOCUMENTS

| | | | |
|---|---|---|---|
| 2011/0270245 A1* | 11/2011 | Horner | ............... A61B 18/1445 606/41 |
| 2012/0116262 A1 | 5/2012 | Houser et al. | |
| 2014/0039315 A1* | 2/2014 | Davies | ............... A61B 18/1477 604/528 |
| 2017/0333115 A1 | 11/2017 | Schwarz | |

FOREIGN PATENT DOCUMENTS

| | | | |
|---|---|---|---|
| DE | 4222769 A1 | 1/1994 | |
| DE | 102014116065 A1 | 5/2016 | |
| DE | 102020118130 A1 | 1/2022 | |
| WO | WO-2004112621 A1 * | 12/2004 | ......... A61B 18/1445 |

OTHER PUBLICATIONS

Written Opinion for International Application No. PCT/EP2022/066938, mailed Oct. 6, 2022.
International Preliminary Report on Patentability for International Application No. PCT/EP2022/066938, mailed Jan. 4, 2024.

* cited by examiner

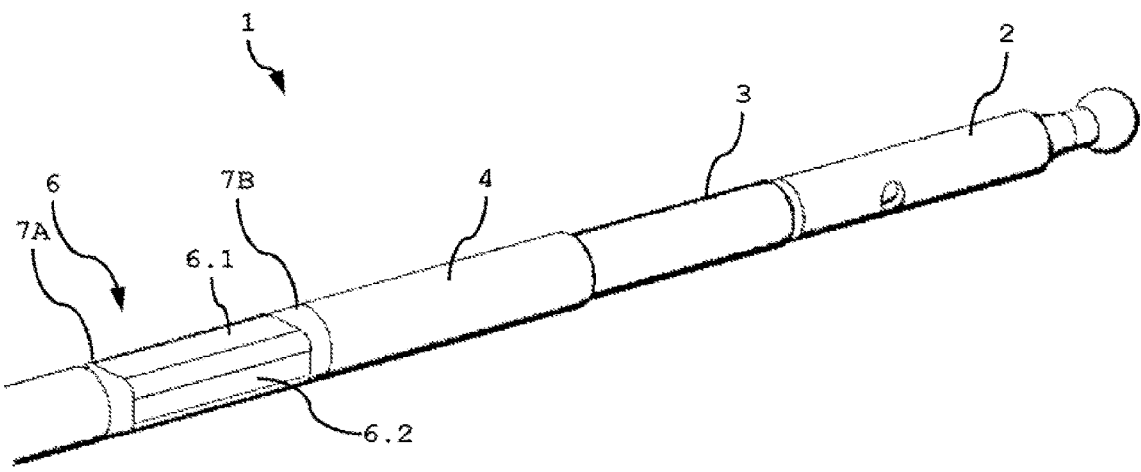
Fig. 5
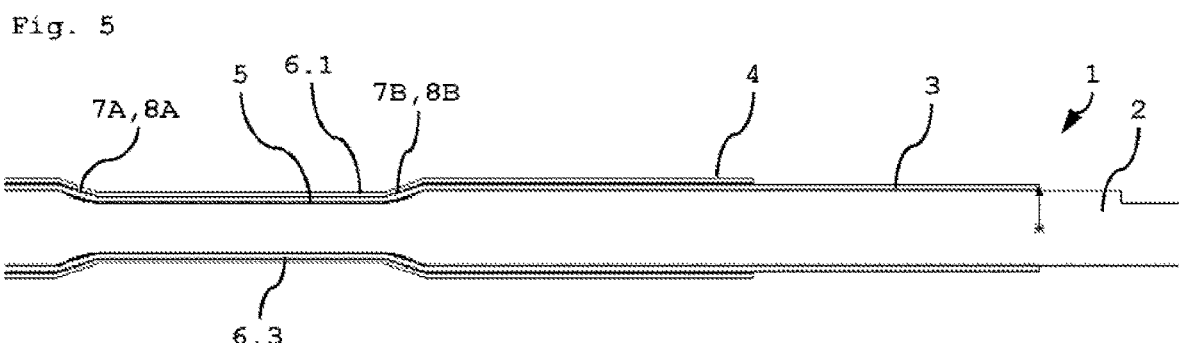
Fig. 6A
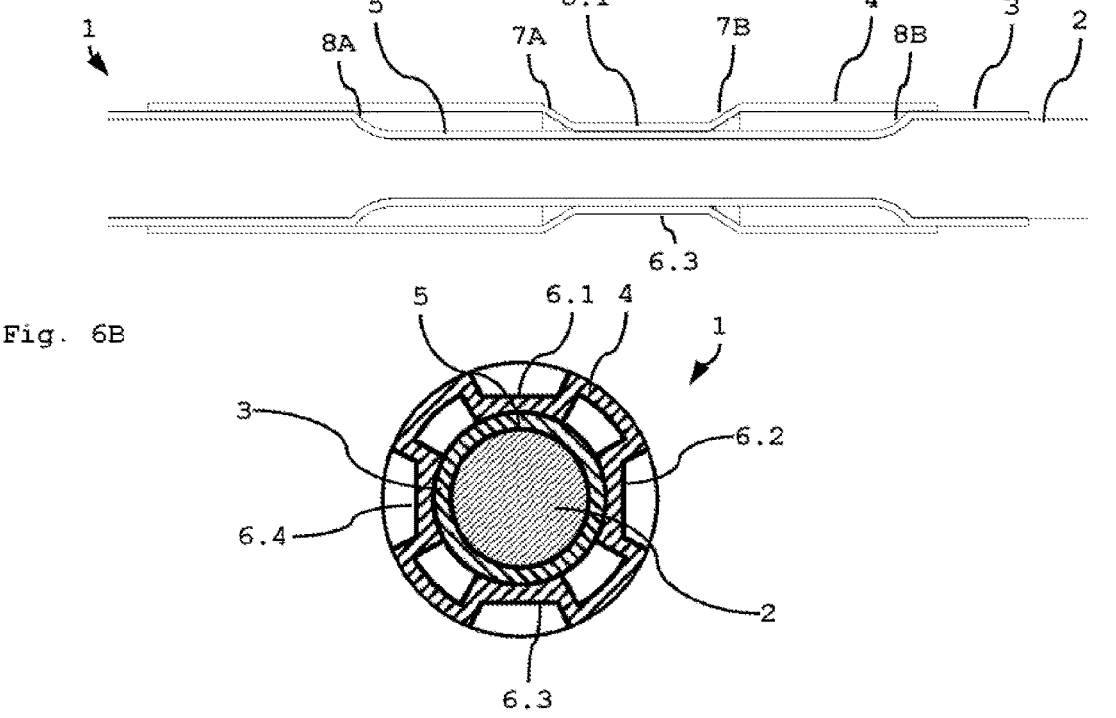
Fig. 6B
Fig. 6C

ACTUATING ELEMENT, SURGICAL INSTRUMENT, AND METHOD FOR MANUFACTURING THE ACTUATING INSTRUMENT

CROSS REFERENCE TO RELATED APPLICATIONS

This application is a national stage application and claims priority 35 U.S.C. 371 to PCT Application No. PCT/EP2022/066938 having an international filing date of 22 Jun. 2022, which designated the United States, which PCT application claimed the benefit of German Patent Application No. 10 2021 116 216.5 filed 23 Jun. 2021.

SCOPE OF THE INVENTION

This invention pertains to a force transmission element with combined mechanical support and electrical isolation, as well as a surgical instrument comprising the force transmission element and a method for manufacturing the force transmission element.

TECHNICAL BACKGROUND

Surgical instruments often have a mechanical support, particularly an anti-rotation lock or an axial guide with a stop. In addition, surgical instruments are often also equipped with electrical isolation (insulation). The mechanical support and electrical isolation are implemented using separate components or elements of the surgical instrument.

For example, surgical tubular shank instruments (e.g., endoscopic instruments) with a tubular shank and a force transmission element inside it are equipped with an anti-rotation lock that prevents the force transmission element from twisting with respect to the tubular shank. In addition, these types of surgical tubular shank instruments may also or alternatively be equipped with an axial guide with a stop that guides the force transmission element in the tubular shank, preferably centrally, in the axial direction and restricts its translational motion by means of one or two stops.

Other examples include bipolar surgical tubular shank instruments (e.g., endoscopic instruments with bipolar implements/accessories) equipped with two electrical conduc-tors that are usually comprised of two components or elements of the surgical tubular shank instrument that are electrically insulated from each other. In the case of bipolar-driven surgical tubular shank instruments, two electrodes (active electrode and neutral electrode) are arranged on the accessories of the surgical tubular shank instrument. In this way, high-frequency alternating current can be applied from a first electrode (active electrode) into the target tissue directly across from the second electrode (neutral electrode).

In the case of bipolar-driven surgical tubular shank instruments with one shank that is designed as the first electrical conductor, and a force transmission element placed inside it that is designed as the second electrical conductor, the design includes an anti-rotation lock or axial guide for the force transmission element on the one hand, and a separate electrical isolation or insulation separating the force transmission element from the tubular shank on the other. Additional individual parts and connections are arranged in this way on these types of surgical tubular shank instruments so that both func-tions, the mechanical guide and the electrical isolation, can be implemented.

SUMMARY OF THE INVENTION

Given the foregoing, the problem addressed by this invention is to produce an improved medical instrument with combined mechanical support and electrical isolation.

This problem is addressed according to the invention by an actuating element characterized by the features of the claims appended hereto and/or by a surgical instrument, and/or by a method with the features of the claims appended hereto. Accordingly, and in accordance with the first aspect of the invention described herein, a force transmission element for surgical instruments is equipped with a rod, electrical insulation, and a sleeve. The rod is electrically conductive and designed to transmit force. The electrical insulation extends circumferentially over an outer surface and at least in sections in the axial direction along the rod. The sleeve is electrically conductive. The sleeve is circumferentially arranged around the electrical insulation and extends at least in sections in the axial direction along the electrical insulation. The rod has at least one recess. The insulation extends at least along the recess. The sleeve has an embossment that extends at least in sections into the recess and which is designed to mesh with a securing element of a surgical instrument.

Moreover, in accordance with a second aspect of the invention described herein, a surgical instrument, in particular a surgical tubular shank instrument, has a force transmission element according to the first aspect of the invention described herein, a tubular shank, a securing element, an implement, and an actuating interface. The force transmission element is housed in the tubular shank. The securing element is supported in the tubular shank and engages the embossment of the sleeve of the force transmission element. The implement can be moved by means of the force transmission element. The actuating interface is designed to actuate the force transmission element.

In addition, in accordance with a third aspect of the invention described herein, a method for manufacturing a force transmission element for surgical instruments, in particular a force transmission element according to the first aspect of the invention described herein, is specified that includes the following steps:

Preparation of an electrically conductive rod designed to transmit force that has a recess.

Application of electrical insulation circumferentially over an outer surface and at least in sections in the axial direction along the rod, so that the insulation extends at least along the recess.

Circumferential arrangement of an electrically conductive sleeve around the insulation at least in sections in the axial direction along the electrical insulation.

Stamping of an embossment extending at least in sections into the recess and designed to engage with a securing element of a surgical instrument into the sleeve.

The rod can be manufactured at least partially from a metal-lic material such as steel or stainless steel. The rod can be specifically designed to transfer a force in the axial direction (pull or push) as well as or alternatively to transfer torque. The force in the axial direction or the torque can be transferred by the actuating interface to the rod and further transferred through the rod to an accessory or implement of the surgical instrument in order to move the accessory or implement.

The purpose of the recess in the rod is to limit or block at least a translational or rotational degree of freedom of the rod versus the sleeve. In this case, the rod is supported and also or alternatively guided in the area of the recess and the embossment that engages with it. The recess can be made in the rod using a machining procedure such as milling.

The insulation can be manufactured at least in part from a polymer material such as polytetrafluoroethylene (PTFE, Tef-lon) or a ceramic material. The insulation electrically sepa-rates the electrically conducting rod from the electrically conducting sleeve. Particularly in the case of bipolar operation of the surgical implement, the electrical current can be routed over the force transmission element by connecting one of the two poles to the electrical current conductor with the rod and the other of the two poles to the electrical current conductor with the sleeve that is electrically isolated from the rod by the electrical insulation.

The insulation is arranged circumferentially on the surface of the rod. The insulation is thus arranged at least in one section along the rod that extends at least over part of the recess. The insulation contacts the surface of the rod and the insulation is also in contact with the surface of the recess or rod in the area of the recess. Specifically, the insulation is permanently connected mechanically (e.g., press fit) to the rod. The insulation is thus applied to the rod in such a way that it circumferentially encloses the rod at least in the area of the recess. The application can be done for example by means of a coating or shrinking a shrink-sleeve onto it. The insulation can have an essentially uni-form thickness along the circumference of the rod. Accordingly, the embossment of the sleeve extends into the recess in such a way that the embossment comes into contact with the insulation, but not with the rod.

The sleeve can be manufactured at least partially from a me-tallic material such as steel or stainless steel. The sleeve is circumferentially arranged with insulation in an area around the rod that encompasses at least one section of the recess. The drill-hole in the sleeve in the axial direction is specifically concentrically arranged. The sleeve is either permanently connected to the insulation mechanically (e.g., press fit) or allows for sliding or rotation of the rod with the insulation with respect to the sleeve with a predefined sliding friction (e.g., loose fit) in the sleeve drill hole. To do this, the sleeve is pushed onto the rod and advanced until it is at least partly arranged in the area of the recess.

The embossment is pressed into the sleeve in such a way that the embossment engages in the recess, with the embossment coming into contact only with the insulation around the rod, and not with the rod itself. In particular, the embossment engages in the recess in the radial direction. The embossment and the recess thus form a support or guide for the rod vis-à-vis the sleeve, with the insulation in contact with both and both isolated from each other. The rod is therefore supported or guided with the insulation in the sleeve at least in the area of the recess and the embossment that engages in it. The stamping of the sleeve can be done using a punch in a predefined section of the circumference of the sleeve or all the way around it by roll-pressing.

The force transmission element is pushed into the tubular shank of the surgical instrument. During this process, the force transmission element is supported or guided in the tubular shank at least through the sleeve. The sleeve can be electrically insulated with respect to the tubular shank. In particular, the sleeve is supported or guided in the tubular shank in such a way that it or the force transmission element can move axially or rotate with respect to the sleeve. The force transmission element can thus transfer an axial force (push or pull) as well as or alternatively a torque within the tubular shank and relative to it.

To prevent any unwanted movement or twisting of the force transmission element with respect to the tubular shank that could lead, for example, to the force transmission element sliding out of the tubular shank, the sleeve and with it the force transmission element are secured in the tubular shank by the securing element. The securing element supported in the tubular shank does this by engaging in the embossment of the sleeve. For example, the securing element can be movably supported in the radial direction vis-à-vis the tubular shank and engage in the embossment in the radial direction. In particular, the securing element can be pre-tensioned in the radial direction, e.g., using an elastic spring lock washer.

The implement, which can specifically be designed in the form of a removable accessory, is moved by means of the axial force or torque that is transmitted via the force transmission element inside and with respect to the tubular shank. The implement can be designed as a clamp, forceps, tweezers, gripper, scissors, and the like. In particular, the implement can also be designed for bipolar operation, for example in order to cut or destroy tissue and the like.

The actuating interface is used to actuate the force transmission element by applying an axial force or torque to the force transmission element.

When the surgical instrument is guided by a user such as a surgeon, the surgical instrument includes a grip that serves as a handle for the user. The actuating interface then transmits a force or torque that is applied by the user at the handle using a suitable actuation (e.g., movable grip) to the force transmission element.

In cases where the surgical instrument is to be connected to a robot, the surgical instrument includes a corresponding connection interface for the robot that can apply an axial force or torque via the actuating interface to the force transmission element.

The force transmission element with rod, insulation, and sleeve according to the invention can be manufactured quite easily, since the insulation is only applied to the rod, the sleeve is then arranged on it, and then the embossment has to be punched in the area of the recess of the rod. In addition, the force transmission element according to the invention makes it possible to dispense with a separate component for guiding and electrically insulating the force transmission element with respect to the tubular shank of the surgical instrument. This has the benefit of avoiding increased pro-duc-tion and manufacturing costs that result from additional individual parts and connections. Moreover, there is also the benefit of avoiding failure of the surgical tubular shank instrument in question due to mechanical loading of the afore-said connections that are usually subjected to heavy mechanical demands.

Advantageous enhancements and elaborations of the invention described herein are the subject of the corresponding depend-ent patent claims.

According to one enhancement of the invention described herein, the rod of the force transmission element is designed as a round bar. The electrical insulation extends at least in sections circularly along the surface of the rod. The sleeve is designed as a round tube and extends at least in sections circularly along the surface of the electrical insulation.

According to another enhancement, the tubular shank is designed as a round tube. The rod of the force transmission element is designed as a round bar. The electrical insulation extends at least in sections circularly along the surface of the rod. The sleeve is designed as a round tube and extends at least in sections circularly along the surface of the electrical insulation. The force transmission element is concentrically arranged in the tubular shank.

The rod designed as a round bar has an essentially circular cross-section with essentially constant diameter along the axial direction, except in the area of the recess.

The insulation is, particularly opposite the recess, arranged circularly and specifically concentrically around the rod.

The sleeve designed as a round tube has an essentially circular cross-section with essentially constant diameter along the axial direction, except in the area of the emboss-ment. The sleeve designed as a round tube is arranged in a circular and specifically concentric arrangement around the insulation.

The tubular shank designed as a round tube has an essentially circular cross-section with essentially constant diameter along the axial direction. The force transmission element with rod designed as a round tube and sleeve designed as round tube is concentrically arranged in the tubular shank designed as a round tube. In this case, the securing element engages in the embossment in the radial direction in order to secure the force transmission element with the rod designed as a round bar and the sleeve designed as a round tube in the tubular shank designed as a round tube.

The force transmission element and surgical instrument designed in this way are advantageous in that they are especially easy to manufacture.

According to one enhancement, the embossment is designed to block at least the rotational degree of freedom around an axis parallel to the sleeve or the axial direction of the sleeve upon engagement of a securing element.

The securing element of the surgical element engages in the embossment in such a way that it blocks the rotation of the sleeve and, depending on the design of the recess, the rod as well vis-à-vis the tubular shank. This limits the movement to an axial advance of the sleeve and, depending on the design of the recess, the rod as well with respect to the tubular shank.

This makes it possible to prevent unwanted rotations of the sleeve or the entire force transmission element as well vis-à-vis the surgical element implement or accessory, thus ensuring trouble-free operation of the implement/accessory.

According to an enhancement, the embossment has at least one essentially flat section to the essentially flat adja-cent contact of a flat surface of a securing element. The essentially flat section runs parallel to the axial direction of the sleeve and is located radially deeper inside compared to the surface of the sleeve.

The essentially flat section can be produced in the rod or round bar by means of face milling, for example. The essentially flat section forms a flat contact surface. When it comes in (preferably flat) contact with the likewise essen-tially flat surface of the securing element that is pre-ten-sioned inward onto the sleeve in the radial direction, then the sleeve and, depending on the design of the recess, the rod as well are blocked from rotating/twisting against the tubular shank of the surgical instrument.

This embossment design thus offers the advantage of making possible an anti-rotation lock that is particularly easy to manufacture.

According to an enhancement of the invention described herein, the recess has at least one essentially flat section parallel to the axial direction of the rod. The essentially flat section is located further inside in the radial direction versus the outer surface of the rod and fits against the essentially flat section of the embossment, particularly flat against it.

To the extent that the sleeve is secured against rotation or torsion in the tubular shank over the essentially flat section of the embossment and the securing element with the essentially flat surface of the surgical element, the rod is also secured against rotation/torsion across its essentially flat section and across the essentially flat section of the emboss-ment with respect to the tubular shank.

According to an enhancement of the invention described herein, the embossment is designed to limit or block at least the translational degree of freedom in a direction parallel to the sleeve or the axial direction of the sleeve upon engage-ment of a securing element.

The securing element on the surgical element engages in the embossment in such a way that it limits or blocks axial shifting of the sleeve and, depending on the design of the recess, the rod as well vis-à-vis the tubular shank. In one embodiment, this can enable rotation of the sleeve and, depending on the design of the recess, the rod as well with respect to the tubular shank.

This makes it possible to prevent unwanted axial move-ments of the sleeve or the entire force transmission element as well with respect to the surgical element implement or accessory, thus ensuring trouble-free operation of the imple-ment/accessory.

According to an enhancement, the embossment has at least one stop. The stop, of which there is at least one, on the embossment is designed to block or limit at least the translational degree of freedom parallel to the sleeve or the axial direction of the sleeve upon engagement of the secur-ing element.

If the securing element is in contact with the stop on the embossment with at least one of its flanks, then axial movement of the sleeve with respect to the tubular shank (in the direction with the stop toward the securing element) is no longer possible. Specifically, when two stops on the emboss-ment are created directly opposite each other in the axial direction, the axial movement of the sleeve vis-à-vis the tubular shank is at least limited in both axial directions. If the two stops placed directly opposite each other in the axial direction are arranged in such a way that they always abut the two flanks of the securing element that are oriented in the axial direction, then the translational degree of freedom of the sleeve versus the tubular shank is blocked, and not just limited.

According to an enhancement of the invention described herein, the recess has at least one stop. The at least one stop of the recess is designed to limit or block at least the translational degree of freedom in a direction parallel to the rod or to the axial direction of the rod together with the embossment.

When the embossment with its at least one stop fits against the stop in the recess in the axial direction, then axial movement of the rod vis-à-vis the sleeve is no longer possible in the direction with the stop of the recess toward the stop of the embossing. Specifically, when there are two recess stops opposite each other in the axial direction, the axial movement of the rod vis-à-vis the sleeve is at least limited in both axial motion directions. If the two recess stops placed directly opposite each other in the axial direc-tion are arranged in such a way that they contact the two embossment stops in a similar way, then the translational degree of freedom of the rod versus the sleeve is blocked, and not just limited.

According to an enhancement of the invention described herein, the electrical insulation has sliding properties on its outer surface at least in the area of the embossment. In addition or alternatively, the sleeve has sliding properties on its inner surface at least in the area of the embossment.

The sliding properties of the outer surface of the electrical insulation or the inner surface of the embossment can be ensured by choosing the appropriate material (e.g., PTFE for the electrical insulation) and additionally or alternatively by means of suitable treatment of the respective surface (e.g., polishing or honing). For example, the electrical insulation can be manufactured from PTFE and the sleeve from stainless steel. Moreover, the inner surface of the sleeve can be polished. The polished inner surface of the stainless steel sleeve can thus easily slide on the outer surface of the PTFE insulation, enabling a sliding axial movement or rotation of the sleeve vis-à-vis the electrical insulation.

According to an enhancement of the invention described herein, the securing element has sliding properties on its surface facing the embossment. In addition or alternatively, the embossment has sliding properties on its outer surface.

The sliding properties of the surface of the securing element facing the embossment or the outer surface of the embossment can be ensured by choosing the appropriate material and additionally or alternatively by means of suit-able treatment of the respective surface (e.g., polishing or honing). For example, the sleeve and the securing element can be manufactured from stainless steel and the outer surface of the sleeve and the surface of the securing element facing the embossment can be polished. The polished outer surface of the stainless steel sleeve can thus easily slide on the surface of the securing element facing the embossment, enabling a sliding axial movement or rotation of the sleeve with respect to the tubular shank of the surgical instrument.

According to an enhancement of the invention described herein, the preparation step [includes] a step of creating the recess in the rod, especially by reshaping, e.g., pressing, or by machining, e.g., milling or turning.

According to an enhancement of the invention described herein, the step for applying the insulation includes shrink-ing a shrink sleeve on to the rod or coating the rod.

According to an enhancement of the invention described herein, the circumferential arrangement step includes the following steps:

Heating the sleeve until thermal expansion causes the inner diameter of the sleeve to become larger than the outer diameter of the electrical insulation.

Sliding the heated sleeve onto the electrical insulation.

Cooling the heated sleeve that has been pushed on.

The heated sleeve is pushed onto the rod with the elec-trical insulation until it is arranged at least partially in an area of the recess of the rod. As soon as the pushed-on sleeve has cooled, there will be a press fit between the sleeve and the electrical insulation, that is, a fixed mechanical connec-tion, or a loose fit, i.e., a sliding connection.

The designs and enhancements described above can be combined with each other in any number of rational ways. Other possible designs, improvements, and embodiments of the invention also include combinations of characteristics of embodiments of the invention described above or below that have not been explicitly specified. In particular, a person skilled in the art will also add individual aspects as improve-ments or enhancements to the respective basic form of the invention described herein.

CONTENTS OF THE DESIGN

The invention described herein is further explained below with the aid of the embodiments provided in the schematic figures in the drawings.

FIG. 5 shows an isometric view of a second embodiment of the force transmission element;

FIG. 6A shows a lengthwise cross-section of an initial variant of the second embodiment of the force transmission element;

FIG. 6B shows a lengthwise cross-section of a second variant of the second embodiment of the force transmission element;

FIG. 6C shows a cross-section of the second embodiment of the force transmission element in the area of the emboss-ment;

The attached drawing figures are intended to convey further understanding of the embodiments of the invention. They show embodiments and, in connection with the description, serve to explain the principles and concepts behind the invention. Other embodiments and many of the advantages named herein can also be derived from the drawings. The elements of the drawings are not necessarily shown to scale with each other.

In the figures, elements, characteristics, and components that are similar or have an equivalent function or action—unless otherwise indicated—are respectively labeled with the same reference numbers.

DESCRIPTION OF EMBODIMENTS

Figure 1:
FIG. 1 shows a side view of a manually guided surgical instrument.
Figure 1:
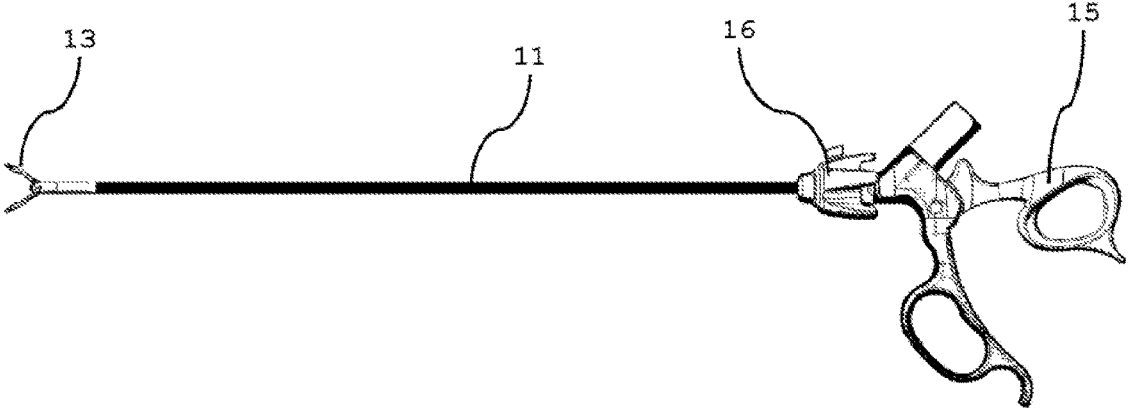

FIG. 1 is a schematic representation of a single manually guided surgical instrument 10. The surgical instrument com-prises a force transmission element (not shown here, see FIGS. 2 to 10), a tubular shank 11, a securing element (not shown here, see FIG. 2), an implement or accessory 13, a handle 14, a movable grip 15, and an accessory interface 16.

Figure 2:
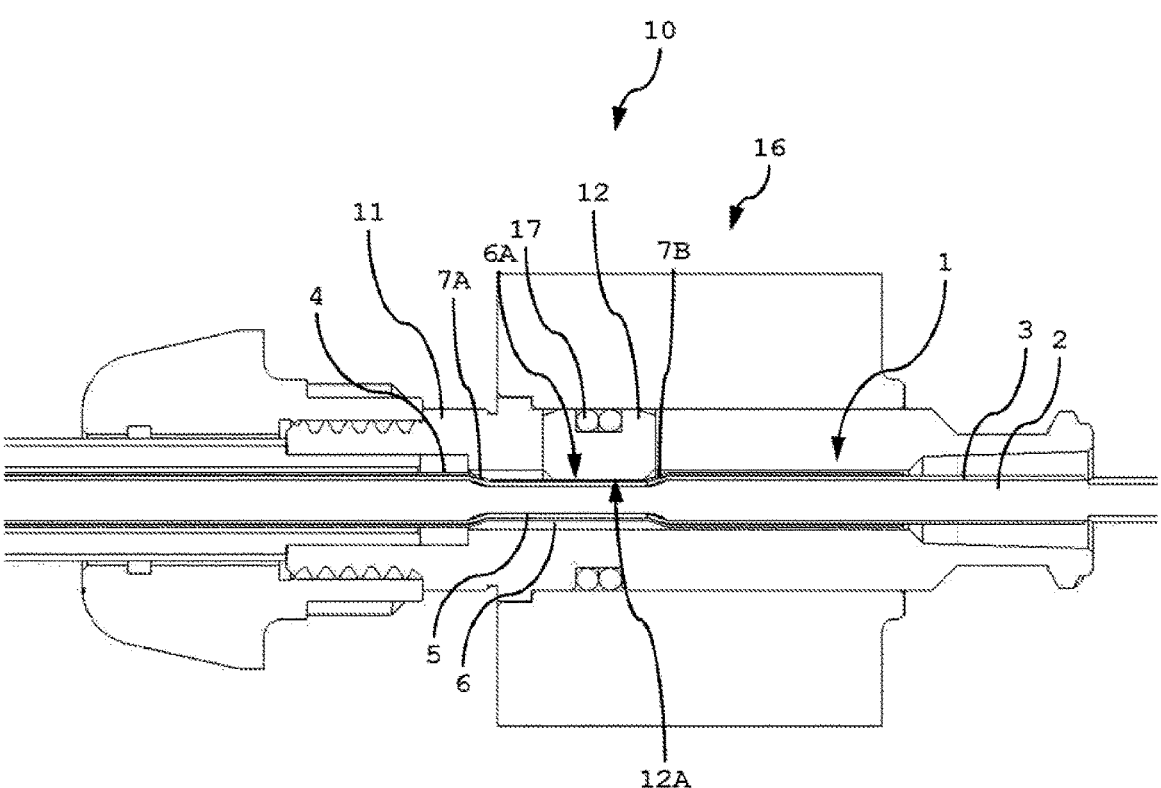
FIG. 2 shows a lengthwise cross-section of the surgical instrument.

The force transmission element is enclosed and supported in the tubular shank 11 (see FIG. 2). The securing element secures the force transmission element against twisting and also or alternatively against axial displacement vis-à-vis the tubular shank 11 (see FIG. 2). The implement 13 is de-picted here as a gripper that can be supplied with bipolar electric current via the force transmission element. The surgical instrument here is fitted with a handle 14 for manual guidance by a user (e.g., surgeon). Alternatively, the surgical instrument 10 can be equipped with an appropriate connection interface (not shown) for a robot for robotic guidance. The movable grip 15 is used for applying force manually. In this process, the force applied to the grip 15 is transmitted through grip 15 to the force transmission element. The force transmission element in turn transmits the axial force to the implement/accessory. In addition, two electrical poles of a bipolar generator (not shown) are connected to the implement via the force transmission element. The implement/accessory 13 can be connected to the handle 14 in a mechanically de-tachable way via the accessory interface 16.

FIG. 2 shows a schematic representation of a lengthwise section through the surgical instrument 10 from FIG. 1 near the accessory interface 16.

The force transmission element 1 is enclosed and guided in the tubular shank 11 implemented as a round tube. In this case, the force transmission element 1 is secured by the securing element 12 guided in the tubular shank 11. The force transmission element 1 is comprised of a rod 2, an electrical insulation 3, and a sleeve 4.

The rod 2 is implemented as a round bar and manufactured from stainless steel. An axial force, such as a force from the movable grip (not shown here, see FIG. 1) can be transmitted via the rod 2 to the implement (not shown here, see FIG. 1). Moreover, one of two electrical poles of the bipolar generator can be connected with the implement via the rod 2. The rod 2 has a recess 5. The recess 5 can take different forms (see FIGS. 3 to 10).

The electrical insulation 3 is manufactured from PTFE and is arranged circumferentially, here in a circular and concentric manner, around the rod. The material could also be PFA or a similar material. The electrical insulation 3 is permanently mechanically connected with the rod 2 and electrically iso-lates the rod 2 from the sleeve 4. The electrical insulation 3 is also arranged in the area of the recess 5 around the rod 2 and is permanently mechanically connected to it.

The sleeve 4 is manufactured from stainless steel and is arranged circumferentially, here in a circular and concentric manner, around the electrical insulation 3. The sleeve 4 has an embossment 6 near the recess 5 that engages in the recess 5. In this case, the sleeve 4 is in contact along its entire length only with the electrical insulation 3, but not with the rod 2. The other of the two electrical poles of the bipolar generator can be connected with the implement via the sleeve 4. The embossment 6 has a distal stop 7A and a proximal stop 7B.

The securing element 12 is pretensioned by means of an annular spring 17 in the distal direction toward the force transmission element 1 and engages in the embossment 6. In this process, a surface 12A of the securing element 12 facing the embossment rests against the exterior surface of the embossment 6. The surface 12A of the securing element 12 facing the embossment can be essentially flat and the exterior surface of the embossment 6 can include an essentially flat section 6A, so that the surface 12A of the securing element 12 facing the embossment lies essentially flat against the essentially flat section 6A of the embossment 6. This blocks the rotational degree of freedom around the longitudinal axis of the sleeve and thus secures the sleeve 4 from rotating/twisting with respect to the tubular shank 11.

A distal flank of the securing element 12 limits the translational degree of freedom of the sleeve in the axial direction together with the distal stop 7A of the embossment

6. A proximal flank of the securing element 12 limits the translational degree of freedom of the sleeve in the axial direction together with the proximal stop 7B of the embossment 6. FIG. 2 shows a schematic representation of the proximal flank of the securing element 12 against the proximal stop 7B of the embossment 6. The sleeve 4 can therefore not be moved any further in the distal direction with respect to the tubular shank 11.

The extent to which the rod 2 is translationally or rotationally limited or blocked with respect to the sleeve 4 depends on the respective embodiment of the force transmission element 1. Four different embodiments of the force transmission element 1 are described below.

FIGS. 3, 4A, 4B, and 4C show schematic representations of a first embodiment of the force transmission element 1.

The recess 5 in the rod 2 runs circularly around it and has both a distal stop on the embossment 5 and a proximal stop on the embossment. By way of example, the recess 5 can be created in the rod 2 by a turning operation.

The electrical insulation 3 runs circularly and concentrically around the rod 2, including near the recess 5.

The embossment 6 in the sleeve 4 runs circularly around it with a distal stop 7A on the embossment 6 and a proximal stop 7B on the embossment 6 and can be shaped by roll-pressing with one or more turning rollers.

Figures 3, 4A, 4B, 4C:
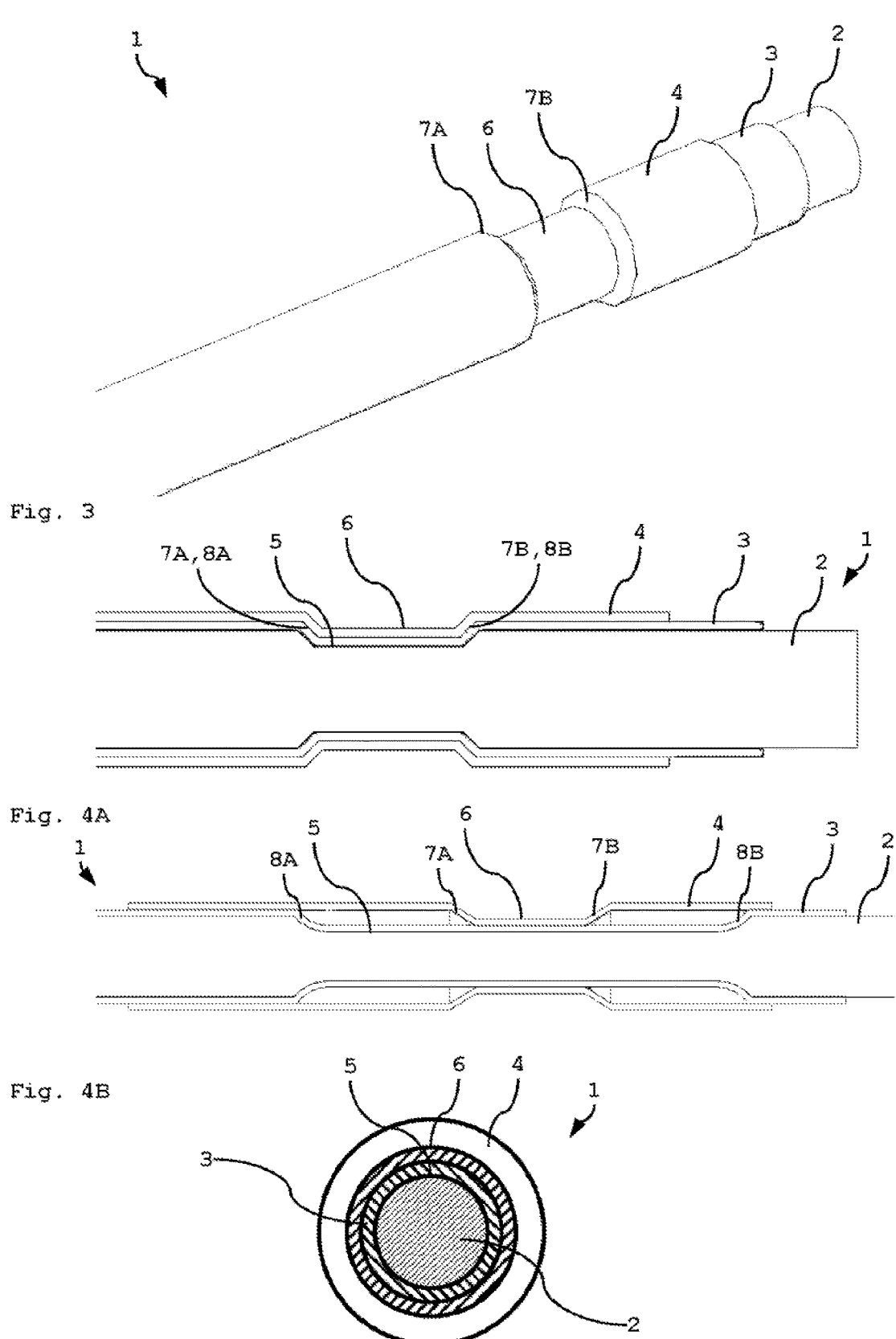
FIG. 3 shows an isometric view of a first embodiment of the force transmission element of the surgical instrument.
FIG. 4A shows a lengthwise cross-section of a first variant of the initial embodiment of the force transmission element.
FIG. 4B shows a lengthwise cross-section of a second variant of the initial embodiment of the force transmission element.
FIG. 4C shows a cross-section of the first embodiment of the force transmission element in the area of the emboss-ment.
Figure 7:
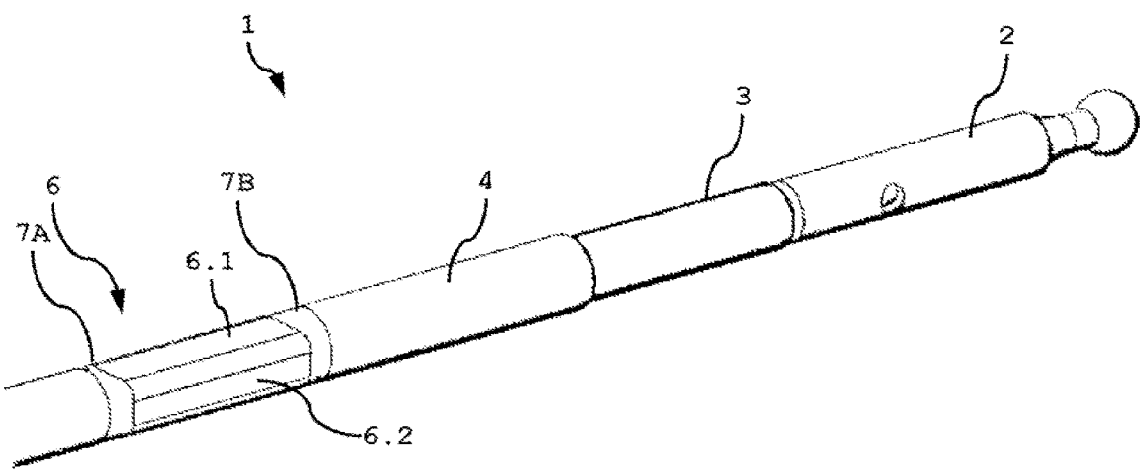
FIG. 7 shows an isometric view of a third embodiment of the force transmission element.

FIG. 4A shows a schematic representation of a lengthwise cross-section through an initial variant of a first embodiment of the force transmission element 1. The sleeve 4 has an embossment 6 that engages in the entire recess 5, with the sleeve 4 resting against the electrical insulation 3. The distal stop 7A on the sleeve 4 rests against a distal stop 8A on the rod 2 or the insulation 3 in this area. Likewise, the proximal stop 7B on the sleeve 4 rests against a proximal stop 8B on the rod 2 or the insulation 3 in this area. The degree of freedom in the axial direction of the rod 2 with respect to the sleeve 4 is thus blocked. Depending on the sliding properties between electrical insulation 3 and sleeve 4, the rod 2 can be rotated with the insulation 3 with respect to the sleeve 4.

FIG. 4B shows a schematic representation of a lengthwise cross-section of a second variant of the first embodiment of the force transmission element 1. The sleeve 4 has an embossment 6 that only engages in one section in the recess 5, with the sleeve 4 resting against the electrical insulation 3. The distal stop 7A on the sleeve 4 does not rest against the distal stop 8A on the rod 2 or the insulation 3 in this area. Likewise, the proximal stop 7B on the sleeve 4 does not rest against the proximal stop 8B on the rod 2 or the insulation 3 in this area. The degree of freedom in the axial direction of the rod 2 is thus only limited to being between the stops, but not completely blocked with respect to the sleeve 4. Depending on the sliding properties between the electrical insulation 3 and the sleeve 4, the rod 2 can be rotated with the insulation 3 with respect to the sleeve 4.

FIG. 4C shows a schematic representation of a cross-section of the first embodiment of the force transmission element 1 in the area of the embossment 6. The embossment 6 rests against the electrical insulation 3 in a circular and concentric manner.

FIGS. 5, 6A, 6B, and 6C show schematic representations of a second embodiment of the force transmission element 1.

The recess 5 in the rod 2 runs circularly around it and has a distal stop in the recess 5 and a proximal stop in the recess 5. By way of example, the recess 5 can be created in the rod 2 by a turning operation.

The electrical insulation 3 runs circularly and concentrically around the rod 2, including in the area of the recess 5.

Here, the embossment 6 in the sleeve 4 has four flat embossments 6.1, 6.2 (two of the four flat embossments are not shown) distributed evenly around the circumference, along with a distal stop 7A for the embossment 6 and proximal stop 7B for the embossment 6. The flat embossments 6.1, 6.2 can be created by, for example, embossing with one or more punches.

FIG. 6A shows a schematic representation of a lengthwise cross-section of a first variant of the second embodiment of the force transmission element 1. The sleeve 4 has four flat embossments 6.1, 6.3 (two of the four flat embossments are not shown) that engage in the entire recess 5, with the sleeve 4 resting against the electrical insulation 3. The distal stop 7A on the sleeve 4 rests against the distal stop 8A on the rod 2 or the insulation 3 in this area. Likewise, the proximal stop 7B on the sleeve 4 rests against the proximal stop 8B on the rod 2 or the insulation 3 in this area. The degree of freedom in the axial direction of the rod 2 with respect to the sleeve 4 is thus blocked. Depending on the sliding properties between the electrical insulation 3 and the sleeve 4, the rod 2 can be rotated with the insulation 3 with respect to the sleeve 4. Rotation can also be blocked in this way.

FIG. 6B shows a schematic representation of a lengthwise cross-section of a second variant of the second embodiment of the force transmission element 1. The sleeve 4 has four flat embossments 6.1, 6.3 (two of the four flat embossments are not shown) that engage in only one section of the recess 5, with the sleeve 4 resting against the electrical insulation 3. The distal stop 7A of the sleeve 4 does not rest against the distal stop 8A of the rod 2 or the insulation 3 in this area. Likewise, the proximal stop 7B of the sleeve 4 does not rest against the proximal stop 8B of the rod 2 or the insulation 3 in this area. The degree of freedom in the axial direction of the rod 2 is thus limited to being only between the stops, but not completely blocked with respect to the sleeve 4. Depending on the sliding properties between electrical insulation 3 and sleeve 4, the rod 2 can be rotated with the insulation 3 with respect to the sleeve 4. Rotation can also be blocked in this way.

FIG. 6C shows a schematic representation of a cross-section of the second embodiment of the force transmission element 1 in the area of the flat embossments 6.1, 6.2, 6.3, and 6.4. The flat embossments 6.1-6.4 rest against the electrical insulation 3 and can be created by, for example, embossing with one or more punches.

A securing element with a flat surface facing the embossment that engages in one of the flat embossments 6.1, 6.2, 6.3, 6.4 blocks the rotational degree of freedom of the sleeve 4, but not of the rod 2 with respect to the tubular shank.

FIGS. 7, 8A, 8B, and 8C show schematic representations of a third embodiment of the force transmission element 1.

The rod 2 in this case has four recesses distributed evenly across the circumference, along with a distal stop in the recess and a proximal stop in the recess. By way of example, the recesses can be created in the rod 2 by a milling operation.

The electrical insulation 3 runs circularly and concentrically around the rod 2, including in the area of the recesses.

Here, the embossment 6 in the sleeve 4 has four flat embossments 6.1, 6.2 (two of the four flat embossments are not shown) distributed evenly around the circumference, along with a distal stop 7A for the embossment 6 and a proximal stop 7B for the embossment 6. The flat embossments 6.1, 6.2 can be created by, for example, embossing with one or more punches.

Figure 8A:
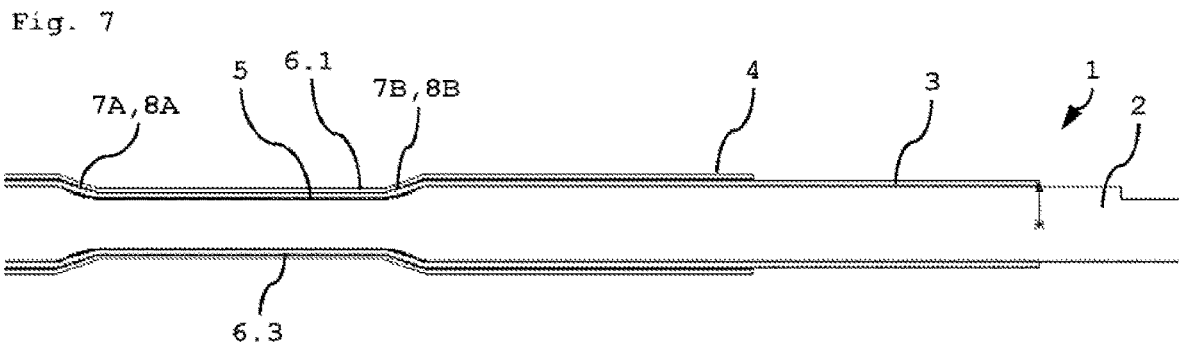
FIG. 8A shows a lengthwise cross-section of a first variant of the third embodiment of the force transmission element.

FIG. 8A shows a schematic representation of a lengthwise cross-section of a first variant of the third embodiment of the force transmission element 1. The sleeve 4 has four flat embossments 6.1, 6.3 (two of the four flat embossments are not shown) that each engage fully in one of the four recesses 5.1, 5.3 (two of the four recesses are not shown), with the sleeve 4 resting against the electrical insulation 3. The distal stop 7A on the sleeve 4 rests against the distal stop 8A on the rod 2 or the insulation 3 in this area. Likewise, the proximal stop 7B on the sleeve 4 rests against the proximal stop 8B on the rod 2 or the insulation 3 in this area. The degree of freedom in the axial direction of the rod 2 with respect to the sleeve 4 is thus blocked. Depending on the sliding properties between the electrical insulation 3 and the sleeve 4, the rod 2 can be rotated with the insulation 3 with respect to the sleeve 4.

Figure 8B:
FIG. 8B shows a lengthwise cross-section of a second variant of the third embodiment of the force transmission element.

FIG. 8B shows a schematic representation of a lengthwise cross-section of a second variant of the third embodiment of the force transmission element 1. The sleeve 4 has the four flat embossments 6.1, 6.3 (two of the four flat embossments are not shown) that each engage in only one section of the corresponding recess 5.1, 5.3 (two of the four recesses are not shown), with the sleeve 4 resting against the electrical insulation 3. The distal stop 7A on the sleeve 4 does not rest against the distal stop 8A on the rod 2 or the insulation 3 in this area. Likewise, the proximal stop 7B on the sleeve 4 does not rest against the proximal stop 8B on the rod 2 or the insulation 3 in this area. The degree of freedom in the axial direction of the rod 2 is thus limited to being only between the stops, but not completely blocked with respect to the sleeve 4. Depending on the sliding properties between the electrical insulation 3 and the sleeve 4, the rod 2 can be rotated with the insulation 3 with respect to the sleeve 4.

Figure 8C:
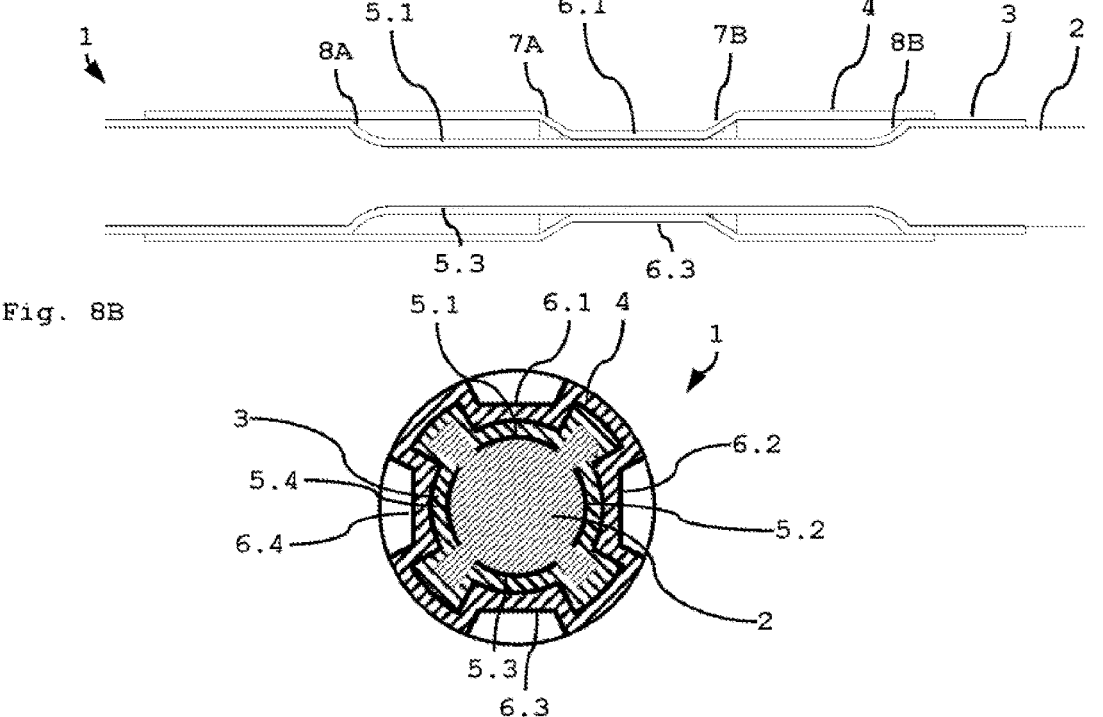
FIG. 8C shows a cross-section of the third embodiment of the force transmission element in the area of the emboss-ment.

FIG. 8C shows a schematic representation of a cross-section through the second embodiment of the force transmission element 1 in the area of the flat embossments 6.1, 6.2, 6.3, and 6.4. The flat embossments 6.1-6.4 engage in the respective recesses 5.1-5.4 and rest against the electrical insulation 3. The flat embossments 6.1-6.4 can be created by, for example, embossing with one or more punches. The recesses can be created by, for example, a milling operation.

A securing element with a flat surface facing the embossment engaging in one of the flat embossments 6.1, 6.2, 6.3, 6.4 blocks the rotational degree of freedom of the sleeve 4, but not of the rod 2 with respect to the tubular shank.

Figure 9:
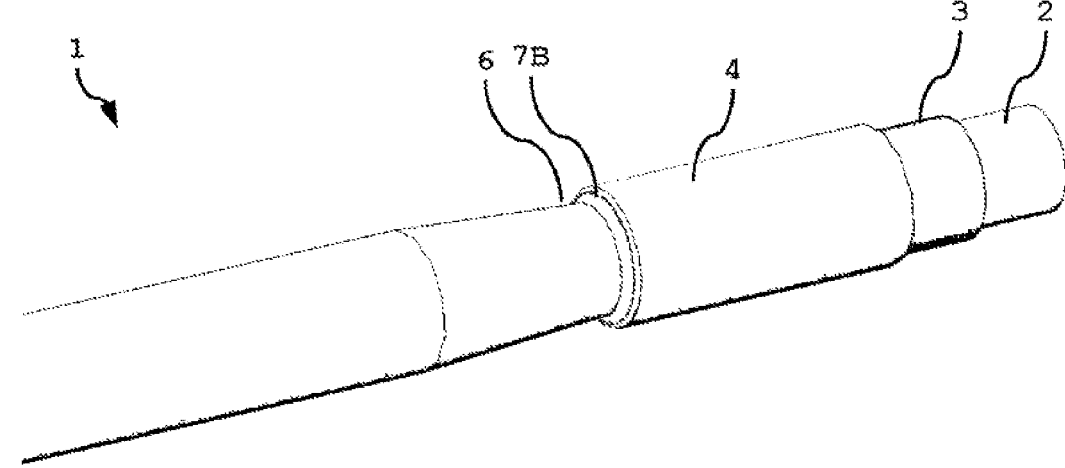
FIG. 9 shows an isometric view of a fourth embodiment of the force transmission element.
Figure 10:
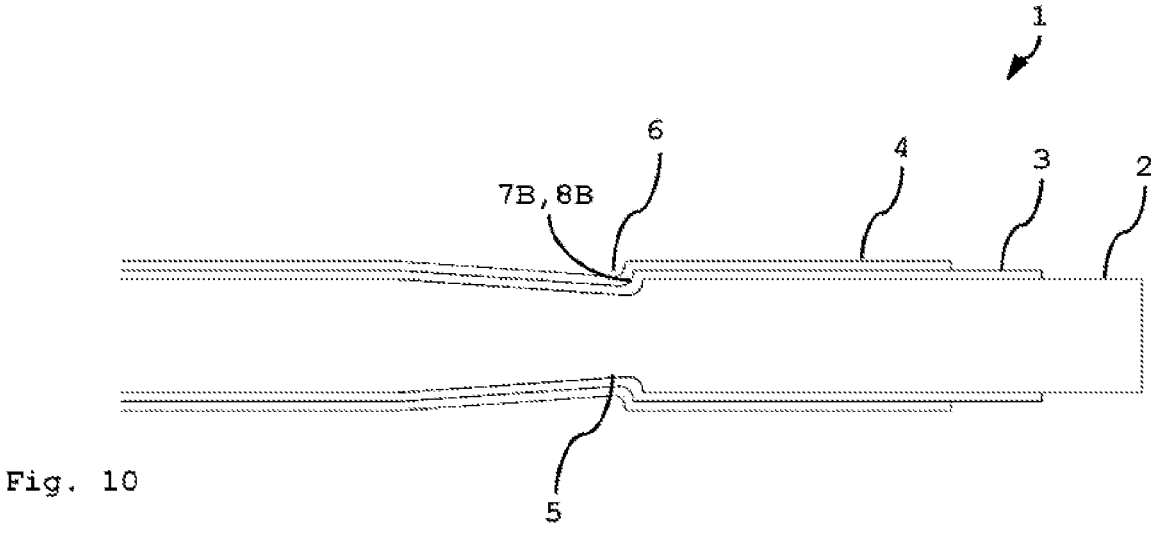
FIG. 10 shows a lengthwise cross-section of the fourth embodiment of the force transmission element.

FIGS. 9 and 10 show schematic representations of a fourth embodiment of the force transmission element 1.

The recess in the rod 2 runs circularly around it and has only a proximal stop in the recess 5. In this case, the recess extends in the distal direction at a predetermined angle with respect to the axial direction. By way of example, the recess 5 can be created in the rod 2 by a turning operation.

The electrical insulation 3 runs circularly and concentrically around the rod 2, including near the recess 5.

The embossment 6 in the sleeve 4 runs circularly around it with only one proximal stop 7B and can, for example, be created by roll-pressing with one or more rollers that are tilted at a corresponding angle with respect to the axial direction.

FIG. 10 shows a schematic representation of a lengthwise cross-section of the fourth embodiment of the force transmission element 1. The sleeve 4 has an embossment 6 that engages in the entire recess 5, with the sleeve 4 contacting the electrical insulation 3. The proximal stop 7B on the sleeve 4 rests against the proximal stop 8B on the rod 2 or the insulation 3 in this area. The degree of freedom in the axial direction of the rod 2 with respect to the sleeve 4 is thus limited in the distal direction, at a minimum. Depending on the sliding properties between the electrical insulation 3 and the sleeve 4, the rod 2 can be rotated with the insulation 3 with respect to the sleeve 4.

Figure 11:
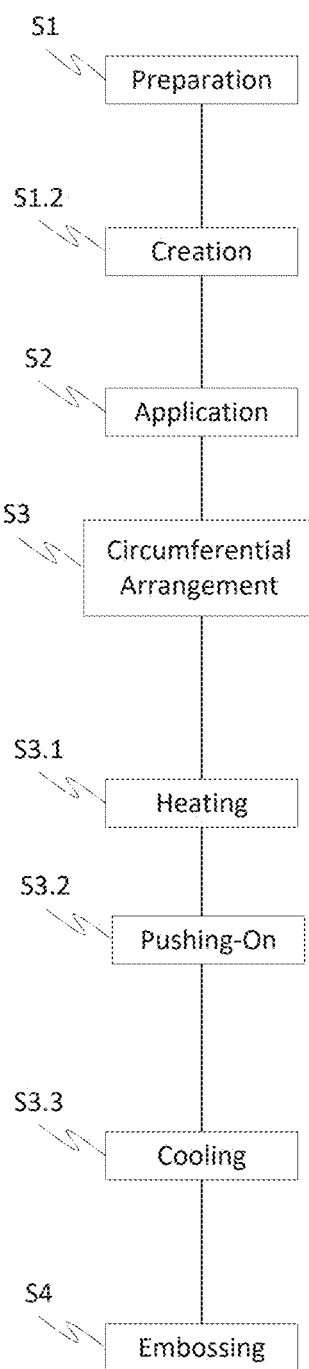
FIG. 11 shows a flow chart of an embodiment of the method for manufacturing a force transmission element.

FIG. 11 shows a schematic representation of an embodiment of the method for manufacturing the force transmission element for surgical instruments, particularly a force transmission element 1 as shown in FIGS. 2 to 10. The method includes the steps of preparation S1, application S2, circumferential arrangement S3, and embossing S3.

In the preparation step S1, an electrically conductive rod designed to transmit force that has a recess is prepared. The preparation step S1 includes the substep of creation S1.2.

In the creation step S1.2, the recess is created in the rod. During this process, the recess is created in particular by reshaping, e.g., pressing, or by machining, e.g., milling or turning. It is possible to create only one (proximal or distal) stop in the recess, optionally in the (distally or prox-imally) running recess, or two stops (proximal and distal) in the recess.

In the application step S2, the circumference of an electrical insulation is wrapped, preferably circularly and particularly preferably, concentrically over an outer surface and at least in sections in the axial direction along the rod in such a way that the insulation extends at least along the recess. The application step S2 specifically includes shrinking a shrink sleeve (e.g., made of PTFE) onto the rod or coating the rod (e.g., with a polymer or ceramic material).

In the circumferential arrangement step S3, an electrically conductive sleeve is arranged around the insulation at least in sections in the axial direction along the electrical insulation, preferably circularly and especially preferably concentrically. The circumferential arrangement step S3 includes the substeps of heating S3.1, pushing on S3.2, and cooling S3.3.

In the heating step S3.1, the sleeve is heated until thermal expansion causes the inner diameter of the sleeve to become larger than the outer diameter of the electrical insulation.

In the pushing-on step S3.2, the heated sleeve is pushed onto the electrical insulation. During this operation, the sleeve is pushed on (in the axial direction) until it is arranged at least in an area above the recess.

In the cooling step S3.3, the heated and pushed-on sleeve is cooled. This can be done, for example, by thermal radiation or convection into calm or moving ambient air or by quenching with a cooling medium.

In the embossing step S4, an embossment engaging at least in sections in the recess and designed to engage with a securing element on a surgical instrument is stamped into the sleeve. The stamping of the embossment in the sleeve can be done by roll pressing using one or more press rollers parallel to the axial direction or tilted with respect to it or by stamping with one or more punches acting on the sleeve in the radial direction.

LIST OF REFERENCE NUMBERS

1 Force transmission element
2 Rod
3 Electrical insulation
4 Sleeve
5 Recess
5.1-5.4 Individual recesses
6 Embossment
6A Essentially flat section
6.1-6.4 Flat embossment
7A-7B Embossment stop
8A-8B Recess stop

10 Surgical instrument
11 Tubular shank
12 Securing element
12A Surface facing the embossment
13 Implement/Accessory
14 Handle
15 Movable grip
16 Accessory interface
17 Annular spring

The invention claimed is:

1. A force transmission element for a surgical instrument comprising:

an electrically conductive rod configured for force transmission;

electrical insulation that extends circumferentially over an outer surface of the electrically conductive rod and at least in sections in an axial direction along the electrically conductive rod, wherein the electrical insulation is connected mechanically to the electrically conductive rod; and an electrically conductive sleeve that is a round tube arranged circumferentially around the electrical insulation and extends at least in sections in the axial direction and along the electrical insulation, wherein the electrically conductive rod has at least one recess and the electrical insulation extends at least along the at least one recess, and the at least one recess is configured to limit or block at least a translational or rotational degree of freedom of the electrically conductive rod with respect to the electrically conductive sleeve, and wherein the electrically conductive sleeve has an embossment that extends at least in sections into the at least one recess and which is configured to mesh with a securing element of the surgical instrument, wherein the embossment is configured to block at least the rotational degree of freedom around an axis parallel to an axial direction of the sleeve when the embossment engages with the securing element, and the embossment has at least one essentially flat section configured to make essentially flat contact with a flat surface of the securing element that runs parallel to the axial direction of the sleeve and is located inwardly in a radial direction with respect to a surface of the electrically conductive sleeve.

2. The force transmission element according to claim 1, wherein the electrically conductive rod is a round bar, where the electrical insulation extends at least in sections circularly along the outer surface of the electrically conductive rod, and wherein the electrically conductive sleeve extends at least in sections circularly along a surface of the electrical insulation.

3. The force transmission element according to claim 1, wherein:

the at least one recess has at least one essentially flat section parallel to the axial direction of the electrically conductive sleeve that is located inwardly with respect to the outer surface of the electrically conductive rod and makes face-to-face or flat face-to-face contact with the essentially flat section of the embossment.

4. The force transmission element according to claim 1, wherein:

the embossment is configured to limit or block the translational degree of freedom in a direction parallel to the electrically conductive sleeve when the embossment engages with the securing element, where the embossment has at least one stop configured to block or limit a translational degree of freedom.

5. The force transmission element according to claim 1, wherein the at least one recess has at least one stop, wherein the at least one stop and the embossment are configured to limit or block at least the translational degree of freedom in a direction parallel to the electrically conductive rod.

6. The force transmission element according to claim 1, wherein one or more of:

the electrical insulation includes on its outer surface and at least in an area of the embossment material configured to allow the electrical insulation to slide, or the electrically conductive sleeve includes materials on its inner surface and at least in the area of the embossment and is configured to slide.

\* \* \* \* \*